United States Patent

Tsuchida

(10) Patent No.: US 9,359,387 B2
(45) Date of Patent: Jun. 7, 2016

(54) ORGANOSILICON COMPOUND HAVING CONJUGATED DIENE STRUCTURE AND MAKING METHOD

(71) Applicant: Shin-Etsu Chemical Co., Ltd., Tokyo (JP)

(72) Inventor: Kazuhiro Tsuchida, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 14/163,525

(22) Filed: Jan. 24, 2014

(65) Prior Publication Data

US 2014/0221678 A1    Aug. 7, 2014

(30) Foreign Application Priority Data

Feb. 7, 2013    (JP) ................................. 2013-021899

(51) Int. Cl.
*C07F 7/08*       (2006.01)
*C07F 7/18*       (2006.01)

(52) U.S. Cl.
CPC . *C07F 7/182* (2013.01); *C07F 7/08* (2013.01); *C07F 7/18* (2013.01); *C07F 7/1876* (2013.01)

(58) Field of Classification Search
USPC .................................................. 556/465, 481
See application file for complete search history.

(56) References Cited

U.S. PATENT DOCUMENTS

| | | | |
|---|---|---|---|
| 5,986,124 A | 11/1999 | Tachikawa et al. | |
| 6,048,994 A | 4/2000 | Tachikawa et al. | |
| 2007/0173935 A1* | 7/2007 | O'Neil et al. | 623/17.11 |

FOREIGN PATENT DOCUMENTS

| | | |
|---|---|---|
| EP | 2 463 291 A2 | 6/2012 |
| JP | 11-180986 A | 7/1999 |
| JP | 2000-143679 A | 5/2000 |

OTHER PUBLICATIONS

Extended European Search Report issued Apr. 15, 2014, in European Patent Application No. 14153293.7.
Hauser et al., "The Wittig Synthesis. I. Use of Certain Aliphatic Aldeydes as Intermediates in the Synthesis of Olefins," The Journal of Organic Chemistry (Feb. 1, 1963), pp. 372-379.
Park et al., "Supporting Information; Gold-Catalyzed Intramolecular Allylation of Silyl Alkynes Induced by Silane Alcoholysis," Journal of the American Chemical Society (Aug. 1, 2006), vol. 128, No. 33, pp. 10664-10665.
Japanese Office Action dated Apr. 21, 2015 for Japanese Application No. 2013-021899 with English translation.
Lappert, "Homogeneous Catalysis", Journal of Organometallic Chemistry, 1974, pp. 425-439, vol. 72, No. 3.
European Office Action for European Application No. 14153293.7, dated Jul. 21, 2015.
Nakadaira et al., "Photochemical isomerization of 1-sila-2,4-cyclohexadiens", Journal of the American Chemical Society, vol. 96, No. 17, Aug. 1, 1974, pp. 5621-5622, XP55202443, ISSN, 0002-7863, DOI, 10.1021/ja00824a078.

\* cited by examiner

*Primary Examiner* — Fereydoun G Sajjadi
*Assistant Examiner* — Pancham Bakshi
(74) *Attorney, Agent, or Firm* — Birch, Stewart, Kolasch & Birch, LLP

(57) ABSTRACT

The invention provides a conjugated diene structure-containing organosilicon compound having formula (1):

$$R^1{}_nX_{3-n}Si\text{-}A\text{-}CR^2\!=\!CR^2\!-\!CR^2\!=\!CH_2 \qquad (1)$$

wherein $R^1$ is a monovalent hydrocarbon group, X is halogen or organoxy, n is 0, 1 or 2, $R^2$ is hydrogen or a monovalent hydrocarbon group, and A is a divalent hydrocarbon group. The organosilicon compound is prepared by reacting a conjugated diene structure-bearing olefin compound with a hydrogensilyl-containing compound in the presence of a platinum catalyst and an acid amide compound, organic amine salt compound, nitrile compound, aromatic hydroxy compound, or carboxylic acid compound.

2 Claims, No Drawings

ORGANOSILICON COMPOUND HAVING CONJUGATED DIENE STRUCTURE AND MAKING METHOD

CROSS-REFERENCE TO RELATED APPLICATION

This non-provisional application claims priority under 35 U.S.C. §119(a) on Patent Application No. 2013-021899 filed in Japan on Feb. 7, 2013, the entire contents of which are hereby incorporated by reference.

TECHNICAL FIELD

This invention relates to an organosilicon compound having a conjugated diene structure and a method for preparing the same.

BACKGROUND ART

Organosilicon compounds having a hydrolyzable silyl group and a reactive organic group are generally referred to as silane coupling agents and often used as adhesives for bonding inorganic-to-organic materials, paint additives, and resin modifiers.

Typical reactive organic groups are vinyl, amino, epoxy, (meth)acrylic, mercapto, isocyanate, ketimine structure, and styryl groups. Silane coupling agents having such groups are well known and used in various applications.

Although silane coupling agents having a conjugated diene structure have not heretofore been reported, they constitute a class of silane materials desired in the butadiene-related industry because the conjugated diene structure is expected to have unique reactivity in contrast to the well-known functional groups.

The reason why the silane materials having a conjugated diene structure have not been reported is that hydrosilylation catalysts used in the synthesis of silane coupling agents are readily deactivated by the conjugated diene structure, failing to produce the desire compound.

Hydrosilylation reaction of adding a compound having silicon-bonded hydrogen to a compound having vinyl group in the presence of a platinum-based catalyst is a well-known technology for the synthesis or modification of organosilanes and organopolysiloxanes and for the silylation of organic compounds and organic polymers. As the means of enhancing reactivity and prohibiting rearrangement of the double bond to control the addition position, Patent Documents 1 and 2 disclose hydrosilylation reaction between a hydrogenalkoxysilane and an aliphatic unsaturated organic compound or vinyl-substituted aromatic compound in the presence of a carboxylic acid compound using a platinum catalyst. These documents relate to ordinary vinyl compounds or vinyl compounds having aromatic conjugation, but do not refer to non-aromatic conjugated dienes.

Needless to say, improvements in reactivity of hydrosilylation lead to improvements in reaction yield and improvements in productivity. When an organosilicon compound hydrosilylated on terminal carbon is used as a coupling agent or modifier, it performs better than an isomer silylated at a non-terminal position. If this organosilicon compound is an organopolysiloxane, it exhibits better physical properties such as heat resistance. Thus, there is a need for a hydrosilylation method for selectively preparing a terminally hydrosilylated organosilicon compound in high yields.

CITATION LIST

Patent Document 1: JP-A 2000-143679 (U.S. Pat. No. 5,986,124)

Patent Document 2: JP-A H11-180986 (U.S. Pat. No. 6,048,994)

DISCLOSURE OF INVENTION

An object of the invention is to provide an organosilicon compound having a conjugated diene structure which is effectively polymerizable and capable of imparting hydrophobic properties, and a method for preparing the organosilicon compound in an efficient manner.

The inventor has found that an organosilicon compound having a specific conjugated diene structure can be produced by the method described below. The organosilicon compound is effectively polymerizable and capable of imparting hydrophobic properties, and has high radical reactivity due to the conjugated diene structure. It is useful as a resin modifier for polyalkylolefin-based polymers, typically elastomers and as a coupling agent for such polymers and inorganic materials.

In one aspect, the invention provides an organosilicon compound having a conjugated diene structure, represented by the general formula (1):

$$R^1{}_n X_{3-n}\text{-Si-A-}CR^2{=}CR^2{-}CR^2{=}CH_2 \tag{1}$$

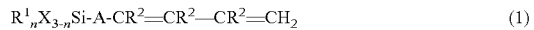

wherein $R^1$ is a monovalent hydrocarbon group, X is halogen or an organoxy group, n is an integer of 0 to 2, $R^2$ is each independently hydrogen or a monovalent hydrocarbon group, and A is a linear, cyclic or branched divalent hydrocarbon group of 4 to 10 carbon atoms. Most often, $R^2$ is hydrogen.

Typical is an organosilicon compound having a conjugated diene structure, represented by the general formula (2):

$$(CH_3)_n(R^3O)_{3-n}\text{-Si-}C_4H_8\text{-}CH{=}CH\text{-}CH{=}CH_2 \tag{2}$$

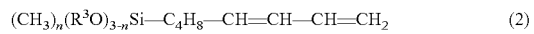

wherein $R^3$ is methyl or ethyl and n is an integer of 0 to 2.

In another aspect, the invention provides a method for preparing an organosilicon compound having a conjugated diene structure, comprising the step of reacting (i) an olefin compound having conjugated diene structure with (ii) a hydrogensilyl-containing compound in the presence of a platinum and/or platinum complex catalyst and at least one compound selected from the group consisting of an acid amide compound, organic amine salt compound, nitrile compound, aromatic hydroxy compound, and carboxylic acid compound.

In a preferred embodiment, the conjugated diene structure olefin compound (i) has the general formula (3):

$$CH_2{=}CH\text{-}B\text{-}CR^4{=}CR^4{-}CR^4{=}CH_2 \tag{3}$$

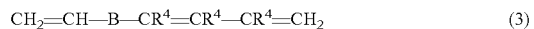

wherein $R^4$ is each independently hydrogen or a monovalent hydrocarbon group, and B is a linear, cyclic or branched divalent hydrocarbon group of 2 to 8 carbon atoms.

Preferably, the acid amide compound has the general formula (4):

$$R^5\text{-}[C({=}O)\text{-}NR^6{}_2]_k \tag{4}$$

wherein $R^5$ is hydrogen or a k-valent hydrocarbon group of 1 to 30 carbon atoms, $R^6$ is each independently hydrogen or a monovalent hydrocarbon group of 1 to 20 carbon atoms, and k is 1 or 2. More preferably, the acid amide compound is a primary acid amide compound having the general formula (5):

$$R^{5'}\text{-}C({=}O)\text{-}NH_2 \tag{5}$$

wherein $R^{5'}$ is hydrogen or a monovalent hydrocarbon group of 1 to 30 carbon atoms.

Preferably the organic amine salt compound is an organic ammonium salt compound having the general formula (6):

$$R^7\text{-}C({=}O)O^-\cdot NH_4^+ \tag{6}$$

wherein $R^7$ is a monovalent hydrocarbon group of 1 to 20 carbon atoms.

In a preferred embodiment, the hydrogensilyl-containing compound (ii) is a silane compound having the general formula (7):

$$H\text{—}SiR^1{}_nX_{3-n} \tag{7}$$

wherein $R^1$ is a monovalent hydrocarbon group, X is halogen or an organoxy group, and n is an integer of 0 to 2, or a hydrolytic condensate of compounds including the silane compound of formula (7). Typically, the hydrogensilyl-containing compound (ii) is trimethoxysilane or triethoxysilane.

Advantageous Effects of Invention

The organosilicon compound having a non-aromatic conjugated diene structure is effectively polymerizable and capable of imparting hydrophobic properties, and has high radical reactivity due to the conjugated diene structure. It is useful as a resin modifier for polyalkylolefin-based polymers, typically elastomers and as a coupling agent for such polymers and inorganic materials.

DESCRIPTION OF EMBODIMENTS

One embodiment of the invention is an organosilicon compound having a conjugated diene structure group, represented by the general formula (1).

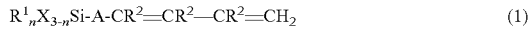

$$R^1{}_nX_{3-n}Si\text{-}A\text{-}CR^2\!\!=\!\!CR^2\text{—}CR^2\!\!=\!\!CH_2 \tag{1}$$

Herein $R^1$ is a monovalent hydrocarbon group, X is halogen or an organoxy group, n is an integer of 0 to 2, $R^2$ is each independently hydrogen or a monovalent hydrocarbon group, and A is a linear, cyclic or branched divalent hydrocarbon group of 4 to 10 carbon atoms.

$R^1$ is a monovalent hydrocarbon group, preferably of 1 to 10 carbon atoms, more preferably 1 to 6 carbon atoms, typically $C_1$-$C_6$ alkyl or aryl. Suitable alkyl groups include methyl, ethyl, propyl, isopropyl, butyl, isobutyl, tert-butyl, pentyl, hexyl, and cyclohexyl. A typical aryl group is phenyl. Of these, methyl is preferred for availability of the precursor.

X is a halogen atom or organoxy group. Suitable halogen atoms include chlorine and bromine, with chlorine being preferred for availability of the precursor. The organoxy group may have 1 to 6 carbon atoms, and examples include alkoxy groups such as methoxy, ethoxy, propoxy and isopropoxy, and alkenoxy groups such as 2-propenoxy. Of these, methoxy and ethoxy are preferred for productivity.

$R^2$ is hydrogen or a monovalent hydrocarbon group, preferably of 1 to 10 carbon atoms, more preferably 1 to 6 carbon atoms. Typical are $C_1$-$C_6$ alkyl groups, examples of which include methyl, ethyl, propyl, isopropyl, butyl, isobutyl, tert-butyl, pentyl, hexyl, and cyclohexyl. Hydrogen is preferred as $R^2$ for availability of the precursor.

"A" is a linear, cyclic or branched, divalent hydrocarbon group of 4 to 10 carbon atoms. Exemplary linear hydrocarbon groups include alkylene groups such as butylene, hexylene, and octylene. A typical cyclic hydrocarbon group is a cyclohexylene-containing group of the following formula.

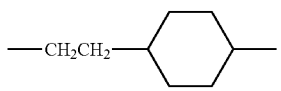

Exemplary branched hydrocarbon groups include alkylene groups having methyl and/or ethyl as a side chain, with the alkylene groups including propylene, butylene, pentylene, hexylene, and octylene. Of these, butylene is preferred for productivity and industrial availability of the reactant.

Specifically, the organosilicon compound having conjugated diene structure is a compound represented by the following formula (2):

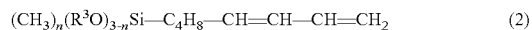

$$(CH_3)_n(R^3O)_{3-n}Si\text{—}C_4H_8\text{—}CH\!\!=\!\!CH\text{—}CH\!\!=\!\!CH_2 \tag{2}$$

wherein $R^3$ is methyl or ethyl and n is an integer of 0 to 2.

Another embodiment of the invention is a method for preparing the organosilicon compound having a conjugated diene structure. The method involves hydrosilylation reaction of (i) an olefin compound having conjugated diene structure with (ii) a compound having hydrogensilyl group in the presence of at least one compound selected from an acid amide compound, organic amine salt compound, nitrile compound, aromatic hydroxy compound, and carboxylic acid compound, using platinum and/or a platinum complex compound as a reaction catalyst. The reactants used in the method are described below.

(i) Olefin Compound having Conjugated Diene Structure

The conjugated diene structure-containing olefin compound is an olefin compound having a conjugated diene structure as typified by a butadiene skeleton, but free of an aromatic structure such as styrene. Specifically, it is an aliphatic compound having a conjugated diene structure and an alkenyl group such as vinyl or allyl, as represented by the following formula (3).

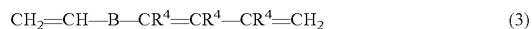

$$CH_2\!\!=\!\!CH\text{—}B\text{—}CR^4\!\!=\!\!CR^4\text{—}CR^4\!\!=\!\!CH_2 \tag{3}$$

Herein $R^4$ is each independently hydrogen or a monovalent hydrocarbon group, and B is a linear, cyclic or branched divalent hydrocarbon group of 2 to 8 carbon atoms.

Examples of the monovalent hydrocarbon group $R^4$ are as illustrated above for $R^2$ in formula (1). B is a linear, cyclic or branched divalent hydrocarbon group of 2 to 8 carbon atoms, examples of which include alkylene groups such as ethylene, butylene, hexylene, and cyclohexylene, and alkylene groups (such as methylene, ethylene, propylene, butylene, and hexylene) having methyl and/or ethyl as a side chain. Of these, ethylene is preferred for productivity and industrial availability of the reactant.

Examples of the compound of formula (3) include 1,3,7-octatriene, 1,3,9-decatriene, 1,3,11-dodecatriene, a compound of formula (8) below, and the foregoing compounds having methyl and/or ethyl introduced as a side chain, but are not limited thereto. Of these, 1,3,7-octatriene is preferred for industrial availability.

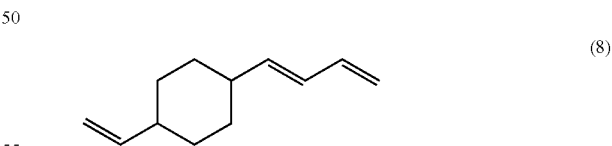

(8)

(ii) Compound having Hydrogensilyl Group

The compound having hydrogensilyl group is a hydrogenhalosilane and/or hydrogenorganoxysilane of the following formula (7):

$$H\text{—}SiR^1{}_nX_{3-n} \tag{7}$$

wherein $R^1$, X and n are as defined above, as well as a hydrolytic condensate of compounds including the hydrogenhalosilane and/or hydrogenorganoxysilane.

The groups represented by $R^1$ and X are as defined and exemplified above. Of these, $R^1$ is preferably methyl because of availability of the precursor and X is preferably methoxy or ethoxy because of availability of the precursor. While the hydrolytic condensate is obtained from the hydrogenalkoxysilane and/or hydrogenorganoxysilane, the condensate may include another constituent compound(s), which is not particularly limited as long as it is an organosilicon compound having an alkoxysilyl group (alkoxy including methoxy, ethoxy and propoxy). The resulting condensate is not particularly limited in its polymer structure, which may be linear, branched or cyclic.

Examples of compound (ii) include, but are not limited to, hydrogentrichlorosilane, hydrogentribromosilane, hydrogentrimethoxysilane, hydrogenmethyldichlorosilane, hydrogenmethyldibromosilane, hydrogenmethyldimethoxysilane, hydrogendimethylchlorosilane, hydrogendimethyibromosilane, hydrogendimethylmethoxysilane, hydrogentriethoxysilane, hydrogenmethyldiethoxysilane, hydrogendimethylethoxysilane, hydrogentri(2-propenoxy)silane, hydrogenmethyldi(2-propenoxy)silane, hydrogendimethyl(2-propenoxy)silane, and hydrolytic condensates of the foregoing silane monomers such as hydrosilyl-containing organopolysiloxanes, organosilsesquioxanes, and cyclosiloxanes (e.g., 1,3,5,7-tetramethylcyclotetrasiloxane), 1,1,3,3-tetramethyldisiloxane, pentamethyldisiloxane, and silicone polymers having a hydrosilyl group at a side chain or end.

The conjugated diene structure olefin compound (i) and the hydrogensilyl-containing compound (ii) are preferably used in such amounts that 0.5 to 1.5 moles, more preferably 0.8 to 1.2 moles of hydrogensilyl compound (ii) is present per mole of olefin compound (i). If the amount of hydrogensilyl compound (ii) used is too small, an excess of olefin compound (i) may be left unreacted. If the amount of hydrogensilyl compound (ii) used is too much, an excess of compound (ii) itself may be left unreacted because of reaction saturation.

The hydrosilylation catalyst includes platinum (Pt) and complex compounds having Pt as the central metal, as is well known in the art. Examples include an alcohol solution of chloroplatinic acid, chloroplatinic acid-1,3-divinyltetra-methyldisiloxane complex and neutralized compound thereof, and 1,3-divinyltetramethyldisiloxane complex having Pt(II) or Pt(0) (i.e., Pt having an oxidation number of 2 or 0) as the central metal. It is preferred from the aspect of selectivity of an addition position that the catalyst be a complex having Pt with an oxidation number exclusive of 4, more preferably 1,3-divinyltetramethyldisiloxane complex having Pt(0) or Pt(II) as the central metal.

The amount of the hydrosilylation catalyst used is not particularly limited as long as it is sufficient to exert catalytic effect on hydrosilylation reaction. The catalyst is preferably used in an amount of 0.000001 to 1 mol %, more preferably 0.0001 to 0.01 mol % based on the olefin compound (i). Less than 0.000001 mol % of the catalyst may be insufficient to exert the catalytic effect. More than 1 mol % of the catalyst may be uneconomical because the catalytic effect may be saturated and the cost of production be increased.

In the practice of the invention, at least one compound selected from among an acid amide compound, organic amine salt compound, nitrile compound, aromatic hydroxy compound, and carboxylic acid compound is used as a hydrosilylation co-catalyst in combination with the hydrosilylation catalyst.

Acid Amide Compound

The acid amide compound used as the hydrosilylation co-catalyst is not particularly limited. It is preferably a carboxylic acid amide compound obtained from an amine and a carboxylic acid and having the general formula (4):

$$R^5—[C(\!=\!O)—NR^6{}_2]_k \quad (4)$$

wherein $R^5$ is hydrogen or a k-valent hydrocarbon group of 1 to 30 carbon atoms, $R^6$ is each independently hydrogen or a monovalent hydrocarbon group of 1 to 20 carbon atoms, and k is 1 or 2. Particularly preferred from the aspect of effectiveness per unit amount is a primary acid amide compound of the general formula (5):

$$R^{5'}—C(\!=\!O)—NH_2 \quad (5)$$

wherein $R^{5'}$ is hydrogen or a monovalent hydrocarbon group of 1 to 30 carbon atoms.

In formula (4), $R^5$ is hydrogen or a mono- or divalent hydrocarbon group of 1 to 30 carbon atoms, preferably 1 to 20 carbon atoms. Examples of the monovalent hydrocarbon group $R^5$ include alkyl groups such as methyl, ethyl, propyl, isopropyl, butyl, hexyl, pentadecyl, heptadecyl and cyclohexyl, aryl groups such as phenyl, and alkenyl groups such as vinyl, but are not limited thereto. Examples of the divalent hydrocarbon group $R^5$ include alkylene groups such as methylene, ethylene and propylene, alkenylene groups such as vinylene, and arylene groups such as phenylene, but are not limited thereto. $R^6$ is each independently hydrogen or a monovalent hydrocarbon group of 1 to 20 carbon atoms, preferably 1 to 6 carbon atoms, examples of which include alkyl groups such as methyl, ethyl, propyl, isopropyl, butyl, hexyl and cyclohexyl and aryl groups such as phenyl, but are not limited thereto. In formula (5), $R^{5'}$ is hydrogen or a monovalent hydrocarbon group of 1 to 30 carbon atoms, preferably 1 to 20 carbon atoms, examples of which are as exemplified above for $R^5$.

Examples of the acid amide compound include formamide, acetamide, N-methylacetamide, N,N-dimethylacetamide, propionamide, acrylamide, malonamide, succinamide, maleamide, fumaramide, benzamide, phthalamide, palmitamide, and stearamide. These are commercially available as reagents. Formamide, acetamide, benzamide and stearamide are preferred from the aspects of availability and co-catalysis.

The amount of the acid amide compound used is not particularly limited as long as it is sufficient to exert co-catalytic effects (reaction promotion and selectivity enhancement). It is preferably used in an amount of 0.00001 to 10 mol %, more preferably 0.001 to 1 mol % based on the conjugated diene structure olefin compound (i). If the amount of the acid amide compound is less than 0.00001 mol %, the catalytic effect may be insufficient. If the amount exceeds 10 mol %, the effects may be saturated and the co-catalyst in excess can rather reduce the catalyst activity.

Organic Amine Salt Compound

The organic amine salt compound used as the hydrosilylation co-catalyst is not particularly limited as long as it is an amine-acid salt compound formed from ammonia or a primary to tertiary amine compound and a carboxylic acid compound. Preferably it is an organic ammonium salt compound of the general formula (6):

$$R^7—C(\!=\!O)^-.NH_4{}^+ \quad (6)$$

wherein $R^7$ is a monovalent hydrocarbon group of 1 to 20 carbon atoms.

In formula (6), $R^7$ is a monovalent hydrocarbon group of 1 to 20 carbon atoms, preferably 1 to 10 carbon atoms. Examples include alkyl groups such as methyl, ethyl, propyl, butyl, pentyl and hexyl, phenyl, and naphthyl.

Preferred examples of the organic ammonium salt compound include ammonium acetate, ammonium propionate, and ammonium benzoate.

The amount of the organic amine salt compound used is not particularly limited as long as it is sufficient to exert co-catalytic effects (reaction promotion and selectivity enhancement). It is preferably used in an amount of 0.00001 to 10 mol %, more preferably 0.001 to 1 mol % based on the conjugated diene structure olefin compound (i). If the amount of the organic amine salt compound is less than 0.00001 mol %, the catalytic effect may be insufficient. If the amount exceeds 10 mol %, the effects may be saturated and the co-catalyst in excess can rather reduce the catalyst activity.

Nitrile Compound

Examples of the nitrile compound serving as the hydrosilylation co-catalyst include acetonitrile, acrylonitrile, propanenitrile, butanenitrile, and benzonitrile. These are commercially available as reagents. Acetonitrile is preferred from the aspects of availability and co-catalytic effects.

The amount of the nitrile compound used is not particularly limited as long as it is sufficient to exert co-catalytic effects (reaction promotion and selectivity enhancement). It is preferably used in an amount of 0.00001 to 20 mol %, more preferably 0.001 to 10 mol % based on the conjugated diene structure olefin compound (i). If the amount of the nitrile compound is less than 0.00001 mol %, the catalytic effect may be insufficient. If the amount exceeds 20 mol %, the effects may be saturated, resulting in a decline of productivity.

Aromatic Hydroxy Compound

Examples of the aromatic hydroxy compound serving as the hydrosilylation co-catalyst include phenol, hydroquinone, cresol, and bisphenol A. These are commercially available as reagents. Phenol is preferred from the aspects of availability and co-catalytic effects.

The amount of the aromatic hydroxy compound used is not particularly limited as long as it is sufficient to exert co-catalytic effects (reaction promotion and selectivity enhancement). It is preferably used in an amount of 0.00001 to 10 mol %, more preferably 0.001 to 10 mol % based on the conjugated diene structure olefin compound (i). If the amount of the aromatic hydroxy compound is less than 0.00001 mol %, the catalytic effect may be insufficient. If the amount exceeds 10 mol %, the effects may be saturated, resulting in a decline of productivity.

Although the nitrile compound and the aromatic hydroxy compound may be used separately, it is preferred for catalyst activating efficiency to use these two compounds together. In this embodiment, the nitrile compound (NC) and the aromatic hydroxy compound (AHC) may be used in a molar ratio (NC/AHC) of 1/1 to 100/1, preferably 10 to 80, and more preferably 20 to 60. If the ratio is less than 1, the reaction may be insufficiently selective and the yield may be reduced because of a more likelihood that ester exchange reaction takes place when the compound having a hydrogensilyl group as one reactant further contains an alkoxysilyl group. If the ratio exceeds 100, co-catalytic effects (reaction promotion and selectivity enhancement) may not be satisfactory. Therefore, the combined use of nitrile compound and aromatic hydroxy compound in an appropriate ratio is recommended.

Carboxylic Acid Compound

The carboxylic acid compound may be any compound having a carboxyl group. Commonly used carboxylic acids include formic acid and acetic acid, which are preferred because of industrial availability.

The amount of the carboxylic acid compound used is not particularly limited as long as it is sufficient to exert co-catalytic effects (reaction promotion and selectivity enhancement). It is preferably used in an amount of 0.00001 to 10 mol %, more preferably 0.001 to 1 mol % based on the conjugated diene structure olefin compound (i). If the amount of the carboxylic acid compound is less than 0.00001 mol %, the catalytic effect may be insufficient. If the amount exceeds 10 mol %, the effects may be saturated and the co-catalyst in excess can rather reduce the catalyst activity.

In the practice of the method, the reaction temperature is preferably in a range of 50 to 150° C., more preferably 60 to 130° C., and more preferably 70 to 110° C. Below 50° C., the reaction rate may be retarded, detracting from productivity. Temperatures in excess of 150° C. may make it difficult to control the addition position, allow addition isomers to form, and invite side reactions such as dehydrogenation of hydrosilyl groups. The reaction time is preferably 30 minutes to 10 hours.

A solvent may be used in implementing the method, if desired. The solvent is not particularly limited as long as it does not interfere with the reaction and is non-reactive with the reactants. Commonly used solvents include alcohol solvents, ether solvents, heteroatom-containing polar solvents, and hydrocarbon solvents. Examples include alcohol solvents such as methanol, ethanol and propanol, ether solvents such as diethyl ether, dimethoxyethane and tetrahydrofuran, heteroatom-containing polar solvents such as acetonitrile and dimethylformamide, aliphatic hydrocarbon solvents such as hexane and heptane, and aromatic hydrocarbon solvents such as toluene and xylene. These solvents may be used alone or in admixture.

The organosilicon compounds having conjugated diene structure are effectively polymerizable and capable of imparting hydrophobic properties, and have good radical reactivity due to the conjugated diene structure. They are thus useful as resin modifiers for polyalkylolefin-based polymers, typically elastomers and as coupling agents for such polymers and inorganic materials.

EXAMPLE

Examples of the invention are given below by way of illustration and not by way of limitation. In Examples, compositional analysis of a reaction product is carried out by using a gas chromatograph with thermal conductivity detector and comparing the chromatogram with the standard compound which has been identified by NMR spectroscopy. The hydrosilylation conversion (%) is determined by analyzing the reaction product by gas chromatography and calculating a ratio of the amount of the hydrogensilyl-containing compound consumed to the initial charge. The platinum complex used is a toluene solution of zero valent platinum-divinylsiloxane complex. In Examples, all parts are by weight.

Example 1

A 500-ml separable flask equipped with a stirrer, reflux condenser, dropping funnel and thermometer was charged with 54.0 parts (0.5 mole) of 1,3,7-octatriene, 0.14 part (0.0033 mole) of acetamide, and an amount (to provide 0.00005 mole of platinum complex (i.e., Pt(0)-1,3-divinyltetramethyldisiloxane complex) per mole of trimethoxysilane to be added dropwise) of the platinum complex toluene solution. The contents were stirred and mixed. The flask was heated until an internal temperature of 60° C. was reached, after which 61.1 parts (0.5 mole) of trimethoxysilane was added dropwise over one hour. The reaction began simultaneously with dropwise addition and was exothermic. As the reaction solution temperature gradually rose from 60° C., heating was stopped. Dropwise addition of trimethoxysilane was continued while controlling such that the reaction solution temperature might not exceed 80° C. After the completion of addition, the reaction solution was ripened for one hour while heating it to keep an internal temperature of 70° C. The contents were analyzed by gas chromatography. The conversion and the chemical composition of the reaction solution are shown in Table 1. Notably, the target compound is an 8-adduct.

Example 2

Reaction was performed as in Example 1 except that triethoxysilane was used instead of trimethoxysilane in Example 1. The conversion and the chemical composition of the reaction solution are shown in Table 1.

Example 3

Reaction was performed as in Example 1 except that methyldimethoxysilane was used instead of trimethoxysilane in Example 1. The conversion and the chemical composition of the reaction solution are shown in Table 1.

Example 4

Reaction was performed as in Example 1 except that formamide was used instead of acetamide in Example 1. The conversion and the chemical composition of the reaction solution are shown in Table 1.

Example 5

Reaction was performed as in Example 1 except that ammonium acetate was used instead of acetamide in Example 1. The conversion and the chemical composition of the reaction solution are shown in Table 1.

Example 6

Reaction was performed as in Example 1 except that acetic acid was used instead of acetamide in Example 1. The conversion and the chemical composition of the reaction solution are shown in Table 1.

Example 7

A 500-ml separable flask equipped with a stirrer, reflux condenser, dropping funnel and thermometer was charged with 54.0 parts (0.5 mole) of 1,3,7-octatriene, 2.95 parts (0.072 mole) of acetonitrile, 0.19 part (0.002 mole) of phenol, and an amount (to provide 0.00005 mole of platinum complex (i.e., Pt(0)-1,3-divinyltetramethyldisiloxane complex) per mole of trimethoxysilane to be added dropwise) of the platinum complex toluene solution. The contents were stirred and mixed. The flask was heated until an internal temperature of 60° C. was reached, after which 61.1 parts (0.5 mole) of trimethoxysilane was added dropwise over one hour. The reaction began simultaneously with dropwise addition and exothermic. As the reaction solution temperature gradually rose from 60° C., heating was stopped. Dropwise addition of trimethoxysilane was continued while controlling such that the reaction solution temperature might not exceed 80° C. After the completion of addition, the reaction solution was ripened for one hour while heating it to keep an internal temperature of 70° C. The contents were analyzed by gas chromatography. The conversion and the chemical composition of the reaction solution are shown in Table 1.

Comparative Example 1

Reaction was performed as in Example 1 except that acetamide was omitted. The conversion and the chemical composition of the reaction solution are shown in Table 1.

TABLE 1

| | Co-catalyst | Conversion, % | Composition of reaction solution, wt % | | |
|---|---|---|---|---|---|
| | | | 8-Adduct (target) | 7-Adduct | 1-Adduct |
| Example 1 | acetamide | 94.2 | 66.5 | 0.3 | 33.2 |
| Example 2 | acetamide | 95.1 | 67.1 | 0.1 | 32.8 |
| Example 3 | acetamide | 94.6 | 65.9 | 0.1 | 34.0 |
| Example 4 | formamide | 95.6 | 68.9 | 0.2 | 30.9 |
| Example 5 | ammonium acetate | 94.3 | 66.5 | 0.4 | 33.1 |
| Example 6 | acetic acid | 95.3 | 65.1 | 0.4 | 34.5 |
| Example 7 | acetonitrile + phenol | 94.0 | 64.8 | 0.5 | 34.7 |
| Comparative Example 1 | none | 8.5 | 21.2 | 5.7 | 73.1 |

The reaction products in Table 1 have the following structure.

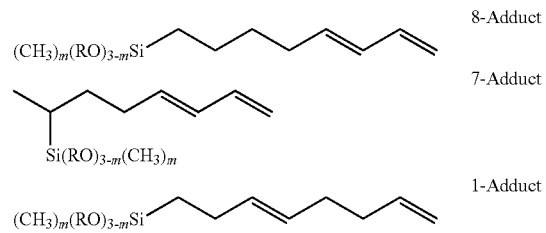

In the formulae, $Si(RO)_{3-m}(CH_3)_m$ wherein R is methyl or ethyl and m is 0 or 1 is a hydrolyzable silyl group.

The results of Examples demonstrate that the inventive method is successful in producing an organosilicon compound having a conjugated diene structure group via hydrosilylation of a non-conjugated olefin terminal carbon at no sacrifice of reactivity while suppressing formation of undesired adduct isomers.

Japanese Patent Application No. 2013-021899 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. An organosilicon compound having a conjugated diene structure of general formula (1):

$$R^1{}_n X_{3-n}\text{-Si-A-}CR^2{=}CR^2{-}CR^2{=}CH_2 \quad (1)$$

wherein $R^1$ is a monovalent hydrocarbon group, X is halogen or an organoxy group, n is an integer of 0 to 2, $R^2$ is hydrogen, and A is a linear, cyclic or branched divalent hydrocarbon group of 4 to 10 carbon atoms.

2. An organosilicon compound having a conjugated diene structure of general formula (2):

$$(CH_3)_n(R^3O)_{3-n}\text{-Si-}C_4H_8\text{-}CH{=}CH{-}CH{=}C_2 \quad (2)$$

wherein $R^3$ is methyl or ethyl and n is an integer of 0 to 2.

* * * * *